United States Patent [19]
Hofmann et al.

[11] Patent Number: 5,702,359
[45] Date of Patent: Dec. 30, 1997

[54] NEEDLE ELECTRODES FOR MEDIATED DELIVERY OF DRUGS AND GENES

[75] Inventors: Gunter A. Hofmann, San Diego, Calif.; Richard A. Gilbert, Tampa, Fla.; Yasuhiko Hayakawa, Ichikawa, Japan; Richard Heller, Brandon; Mark J. Jaroszeski, Tampa, both of Fla.

[73] Assignee: Genetronics, Inc., San Diego, Calif.

[21] Appl. No.: 467,566

[22] Filed: Jun. 6, 1995

Related U.S. Application Data

[63] Continuation-in-part of Ser. No. 42,039, Apr. 1, 1993, Pat. No. 5,439,440.
[51] Int. Cl.$^6$ ........................................... A61N 1/30
[52] U.S. Cl. ...................................... 604/20; 607/116
[58] Field of Search ...................... 604/20–22, 117; 607/37, 116, 148, 53–54

[56] References Cited

U.S. PATENT DOCUMENTS

| | | |
|---|---|---|
| 1,099,062 | 6/1914 | Laposkey . |
| 4,955,378 | 9/1990 | Grasso ................. 128/421 |
| 5,019,034 | 5/1991 | Weaver et al. ............ 604/20 |
| 5,058,605 | 10/1991 | Slovak . |
| 5,128,257 | 7/1992 | Baer ..................... 435/173 |
| 5,273,525 | 12/1993 | Hofmann . |
| 5,389,069 | 2/1995 | Weaver . |

FOREIGN PATENT DOCUMENTS

WO 89/10690  11/1989  WIPO .

*Primary Examiner*—Mark Bockelman
*Attorney, Agent, or Firm*—Baker, Maxham, Jester & Meador

[57] ABSTRACT

An electrode apparatus for the application of electroporation to a portion of the body of a patient, comprises a support member, a pair of electrodes adjustably mounted on the support member for movement toward and away from one another for positioning on opposite sides of a body portion to be electroporated, a sensing element for sensing a distance between the electrodes and generating a distance signal proportionate to the distance between said electrodes, and means responsive to said distance signal for applying pulses of high amplitude electric signal to the electrodes proportionate to the distance between said electrodes.

18 Claims, 6 Drawing Sheets

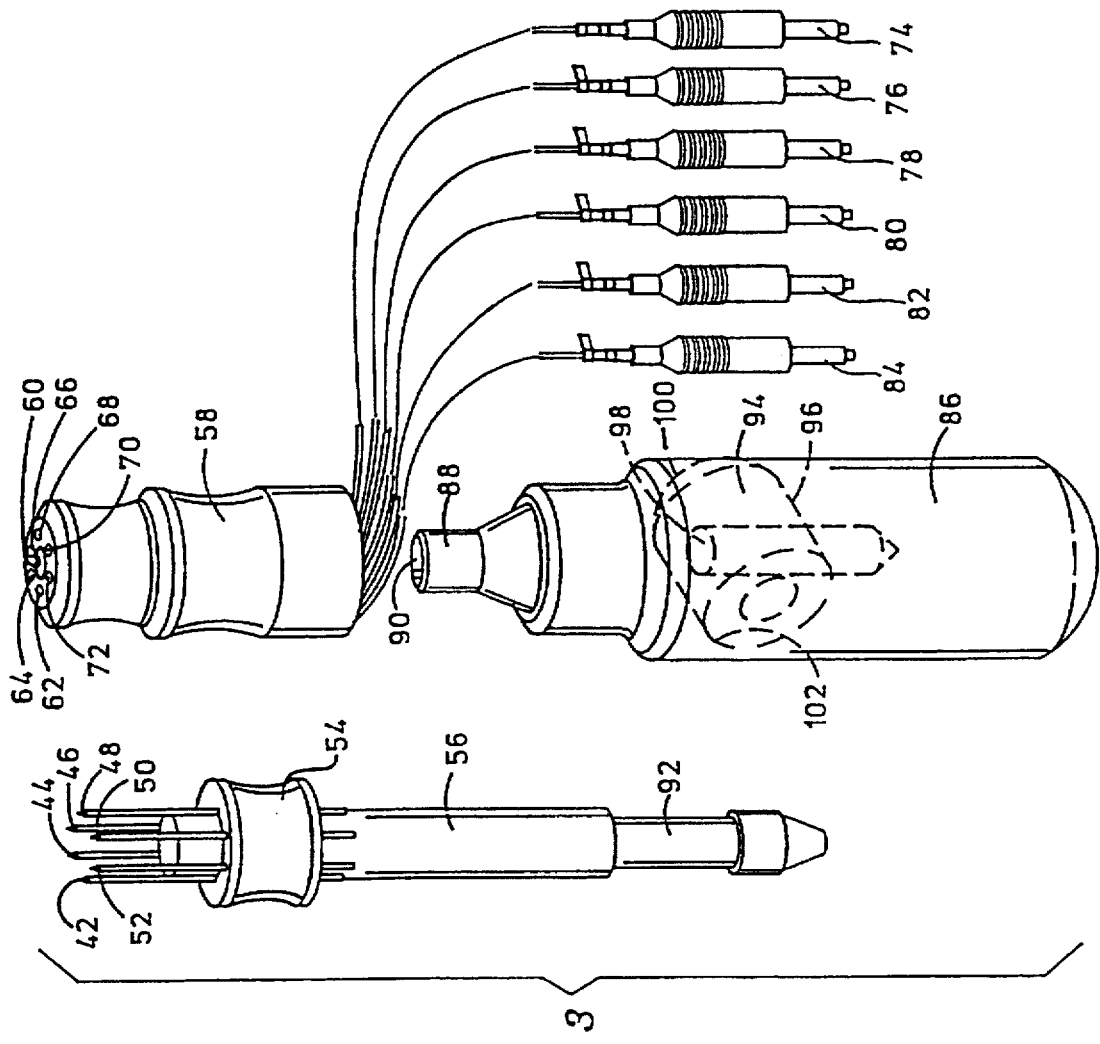
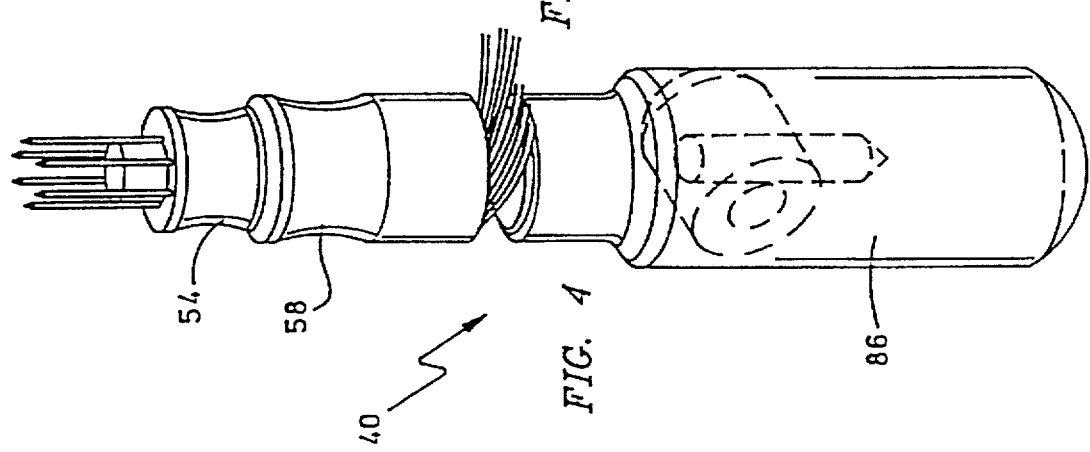

NEEDLE ELECTRODES FOR MEDIATED DELIVERY OF DRUGS AND GENES

REFERENCE TO RELATED APPLICATIONS

The present application is a Continuation-In-Part of application Ser. No. 08/042,039, Filed: Apr. 1, 1993, entitled ELECTROPORATION SYSTEM WITH VOLTAGE CONTROL FEEDBACK FOR CLINICAL APPLICATIONS, now U.S. Pat. No. 5,439,440.

BACKGROUND OF THE INVENTION

The present invention relates to the treatment of ailments in humans and other mammals, and more particularly, to an improved method and apparatus for the application of controlled electric fields for in vivo delivery of genes and pharmaceutical compounds into live cells of a patient by electroporation.

In the 1970's it was discovered that electric fields could be used to create pores in cells without causing permanent damage to them. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells. There they can modify the genome of the cell.

Electroporation has recently suggested as one approach to the treatment of certain diseases such as cancer. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

One therapeutic application of electroporation is for cancer treatment. Experiments on laboratory mammals have been carried out and reported as follows: Okino, M., E. Kensuke, 1990. *The Effects of a Single High Voltage Electrical Stimulation with an Anticancer Drug on in vivo Growing Malignant Tumors.* Jap. Journal of Surgery. 20: 197–204. Mir, L. M., S. Odowski, J. Belehradek Jr., and C. Paoletti. 1991. *Electrochemotherapy Potentiation of Antitumor Effect of Bleomycin by Local Electric Pulses.* Eur. J. Cancer. 27: 68–72. Clinical trials have been conducted and reported by Mir, L. M., M. Belehradek, C. Domenge, S. Orlowski, B. Poddevin, et al. 1991. *Electrochemotherapy, a novel antitumor treatment: first clinical trial.* C.R. Acad. Sci. Paris. 313: 613–618.

This treatment is carried out by infusing an anticancer drug directly into the tumor and applying an electric field to the tumor between a pair of electrodes. The field strength must be adjusted reasonably accurately so that electroporation of the cells of the tumor occurs without damage to any normal or healthy cells. This can normally be easily carried out with external tumors by applying the electrodes to opposite sides of the tumor so that the electric field is between the electrodes. The distance between the electrodes can then be measured and a suitable voltage according to the formula E=V/d can then be applied to the electrodes.

When internal tumors are to be treated, it is not easy to properly locate electrodes and measure the distance between them. In the aforementioned parent application, I disclose a system of electrodes for in vivo electroporation wherein the electrodes may be inserted into body cavities.

It would be desirable to have an electrode apparatus having electrodes that can be inserted into or adjacent tumors so that predetermined electric fields can be generated in the tissue for electroporation of the cells of the tumor.

SUMMARY OF THE INVENTION

Accordingly, it is the primary object of the present invention to provide an improved apparatus that can be conveniently and effectively positioned to generate predetermined electric fields in pre-selected tissue.

It is another principal object of the present invention to provide an improved apparatus that provides an effective and convenient means for positioning electrodes into tissue for the injection of therapeutic compounds into the tissue and application of electric fields to the tissue.

In accordance with a primary aspect of the present invention an electrode apparatus for the application of electroporation to a portion of the body of a patient, comprises a support member, a plurality of needle electrodes adjustably mounted on said support member for insertion into tissue at selected positions and distances from one another, and means including a signal generator responsive to said distance signal for applying an electric signal to the electrodes proportionate to the distance between said electrodes for generating an electric field of a predetermined strength.

Another aspect of the invention includes needles that function for injection of therapeutic substances into tissue and function as electrodes for generating electric fields for portion of cells of the tissue.

BRIEF DESCRIPTION OF THE DRAWINGS

FIG. 3 is an assembly drawing showing a perspective view of an alternate embodiment of the invention.

FIG. 4 is a perspective view of the embodiment of FIG. 3 shown assembled.

DETAILED DESCRIPTION OF THE PREFERRED EMBODIMENTS

As used herein the term "molecules" includes pharmacological agents, genes, antibodies or other proteins. One human therapeutic application of electroporation consists of infusion of an anticancer drug and electroporation of the drug into the tumor by applying voltage pulses between electrodes disposed on opposite sides of the tumor, called electrochemotherapy (ECT). The present invention was devised primarily for enabling ECT such as that reported by Okino and Mir et al to be carded out on non-surface tumors such as those inside the body. However, it may be utilized for other therapeutic applications.

Figures 1, 2:
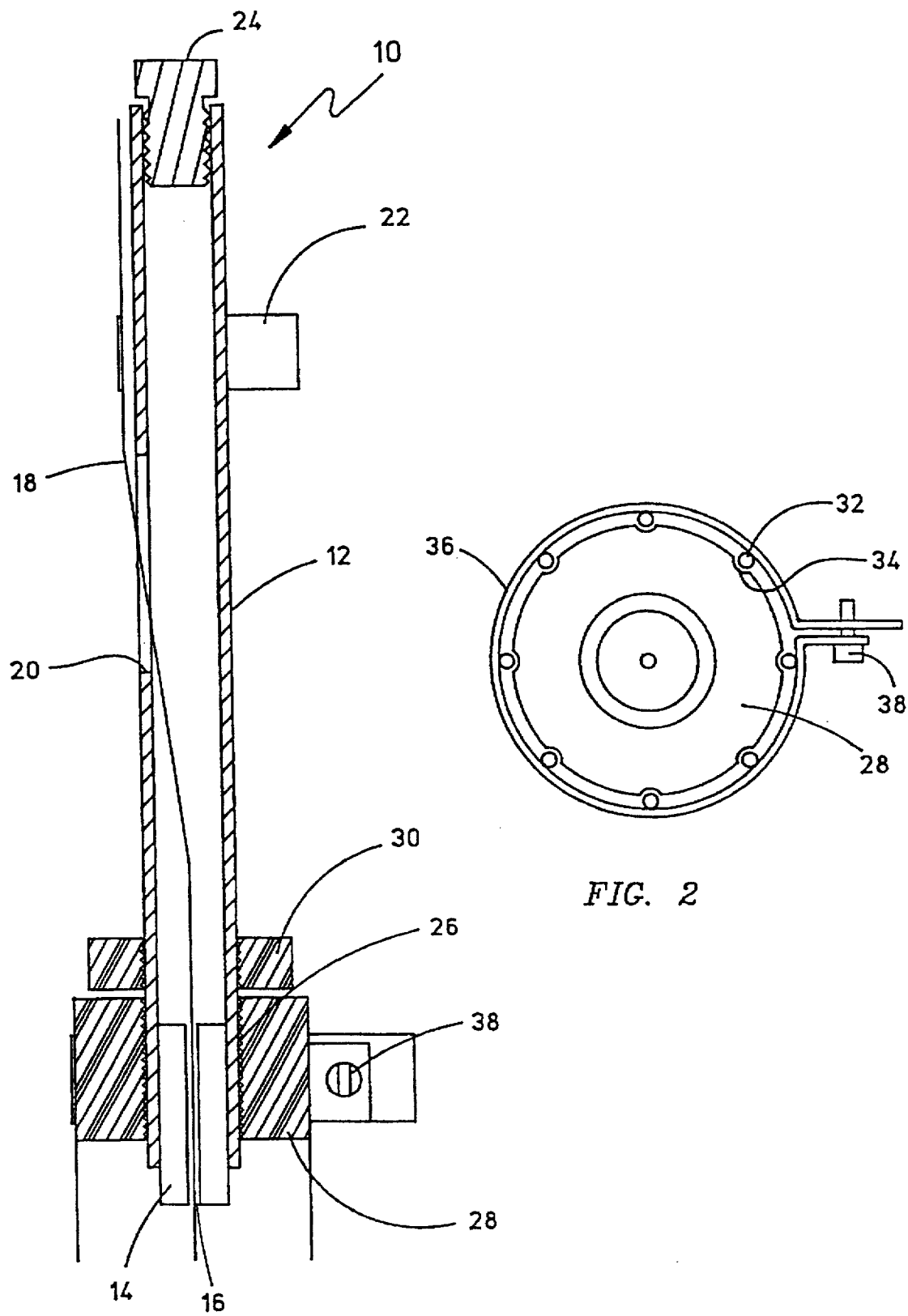
FIG. 1 is a side elevation view, in section of a needle assembly in accordance with a preferred embodiment of the invention.
FIG. 2 is a bottom view of the embodiment of FIG. 1.

Referring to FIG. 1 of the drawings, a needle assembly in accordance with preferred embodiment of the invention is illustrated and designated generally by the numeral 10. The needle assembly comprises an elongated tubular support body 12 which is preferably in the form of a hollow stainless steel shaft. A center needle mount 14 is mounted on the lower end of the shaft 12 and has a central bore 16 for receiving and guiding a center needle 18. The shaft 12 includes a needle exit slot 20 through which the needle electrode 18 extends from the interior thereof to the exterior where it is secured by a clamp 22 to the outside of the tube 12.

The upper end of the electrode 18 may be secured to a screw 24 for connection to an electrical circuit. The lower end of the tubular holder 12 includes threats 26 for threatably receiving a collar 28 for mounting a plurality of needles and a stop collar 30 for stopping or locking the collar 28 in position.

A plurality of needles 32 are mounted in grooves 34 equally spaced around the outer surface of the needle collar 28. This provides a circular array of equally spaced needles, eight in number in the illustrated embodiment. The needles are held in place by a band clamp 36, having the ends clamped together by a screw or nut and bolt 38 which also serves as an electrical connection for the needles. The band clamp 36 directly engages and holds the needles in place.

This new electrode assembly is designed to apply electrical energy to living tissue when the needles are inserted into the tissue. The center needle 18 acts as one electrode, such as an anode or cathode, and the other or annular arrangement of needles 32 functions as the opposite electrode. All of these needles are held in fixed positions when the clamps are installed and secured. One or more of the needles may be cannular or tubular in form for injecting pharmaceutical or other substances into the tissue.

In operation the center needle should be adjusted in order to achieve the desired tissue penetration. This is done by releasing the pressure of the center needle clamp 22 and sliding the center needle 18 outwardly or inwardly, as seen in FIG. 1, so that it extends from the center needle guide 14 to desired penetration distance. The needle is then clamped in position. Thereafter the annular needles 32 are adjusted to achieve the desired penetration into the tissue. This can be accomplished by releasing the pressure of the band clamp 36 and sliding the needles 32 into the desired position. Minor adjustments can also be made by moving the needle collar 28 toward and away from the end of the shaft 12.

After all needles are adjusted to the proper penetration, the shaft 12 is grasped and the needles are inserted into the tissue to the desired depth. Thereafter, a suitable pulse generator is connected to the electrode assembly and the appropriate voltage applied to the electrodes. A suitable quantity of therapeutic substance such as genes or molecules of a suitable chemical or pharmaceutical for treatment of the tissue is injected into the tissue before the voltage is applied.

A modification to this electrode assembly could include a solid non-penetrating electrode (not shown) in place of the center needle. The non-penetrating center electrode could be any suitable shape conductor such as a button or plate attached to the end of the shaft 12 to contact the surface tissue. The annular needle arrangement would be adjusted to penetrate the tissue at the desired depth when the center electrode is resting on a tissue surface. Electrical energy would flow from the penetrating needles through the tissue and to the central electrode on the surface. These arrangements can be utilized to treat near surface tumors where the circular array of electrodes are designed to encircle the tumor. The central electrode is positioned such that the electrical energy flows through the tumor to the central electrode.

Other advantages of this electrode assembly are that all needles 18 and 32 can be independently adjusted to achieve the desired penetration. The needle 28 collar can also be adjusted to position it from the end of the shaft 12 so that insertion of the center and annular needles can be directly observed. In addition, the needle collar 28 can have any size or configuration to suit the tissue area to be treated.

Referring to FIGS. 3 and 4 an alternate embodiment of a circular array needle electrode assembly is illustrated and designated generally by the numeral 40. This needle assembly comprises a circular array of needles 42 through 52, which are mounted in equally spaced relation in a hub 54 mounted on an elongated cylindrical shaft 56. The hub 54 is preferably of a suitably selected diameter to provide the desired diameter of the arrays to position around a tumor or other tissue to be treated. One or more of the needles may be hollow to enable the injection of a medication, as will be more fully described hereinafter.

An electrical connector socket assembly comprises a body member 58 having a central opening or bore 60 for receipt of shaft 56 and an annular array of a plurality of sockets 62 through 72 for receipt of the ends of needles 42 through 52. The sockets 62 through 72 electrically connect the needles to leads 74 through 84 which connect to a distributing switch, as will be subsequently described.

The electrical connector socket 58 fits onto shaft 56 with the end of the needles extending into the electrical sockets 62 through 72 for connecting to the leads 74 through 84. The shaft 56 which mounts the needle array hub 54 and the socket assembly 58 mounts onto a holder 86 adapted to be held in the hand. The holder 86 has an elongated cylindrical configuration adapted to be held in the hand for manipulation. The holder 86 has a forward socket and including a forwardly extending tubular shaft 88 having a bore 90 into which shaft 56 extends while the shaft 88 extends into a bore (not shown) within the connector member 58. The shaft 56 extends into bore 90 and has a annular groove or recess 92 which is engaged by a retainer latch which comprises a transverse plug 94 in a bore 96 biased to one side and including a bore 98 in which the annular slot 92 extends and is retained in the holder. A spring 102 mounted in bore 96 biases plug 94 to the latched position. The shaft 56 may be released for removal by pressing on end 100 of plug 94.

Figure 5:
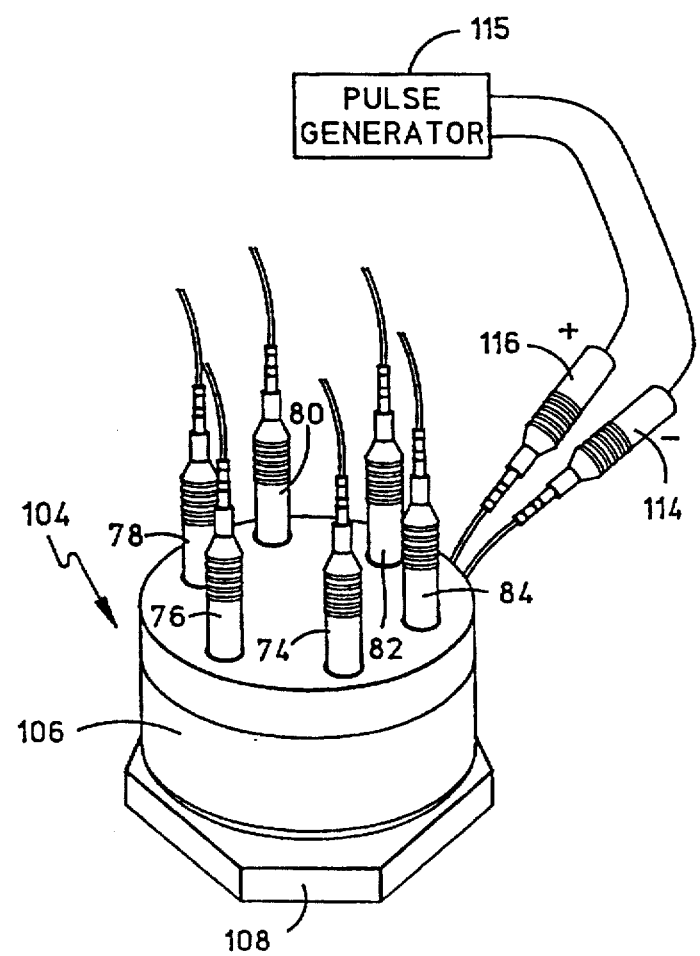
FIG. 5 is a perspective view of a selector switch for the electrode assembly of FIG. 4.
Figure 6C:
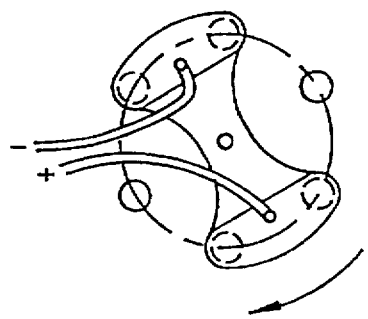

The holder when assembled as shown in FIG. 4 may be grasped in the hand and the needles inserted into a selected tissue area. The needles 42–52 are preferably spaced and positioned to surround the selected tissue of treatment. One or more of the needles 42–52, as previously explained, may be hollow to enable the injection of the desired medication. The electrode leads 74–84 are then connected in a preferred arrangement to a rotatable switch assembly, as shown in FIG. 5, which enables the selection of opposed pairs of the needles for activation or the application of the electrical potential. The switch assembly designated generally by the numeral 104 comprises a stationary housing 106 which, in the illustrated embodiment, is generally cylindrical in configuration and in which is mounted a rotor 108 with spaced contacts 110 and 112 connected by a pair of conductors 114 and 116 to a pulse power generator. The rotor contacts 110 and 112 are positioned within housing 106 to engage annular contacts 118, 120, 122, 124, 126 and 128 to which leads 74–84 are connected.

Figure 6A:
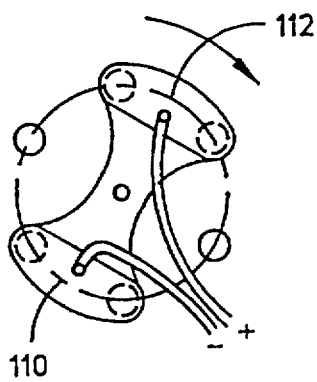
FIGS. 6a–6c is a diagrammatic illustration of selected contact positions of the switch of FIG. 5.
Figure 6B:
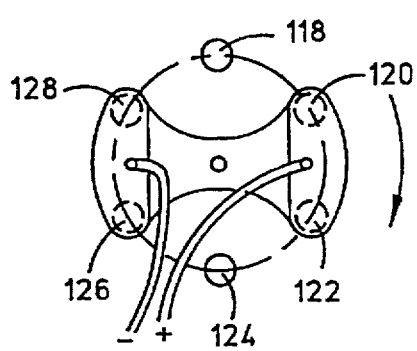

Referring to FIGS. 6a, b and c, the rotor 108 has an internal portion having contacts 110 and 112 each of which bridge between two contacts 118–128 to which the leads 74 through 84 are connected to connect the source of power. The internal contacts 110 and 112 rotate with the rotor 108 and can be selectively positioned in conductive relation with pairs of the internal contacts 118–128 to thereby activate opposed pairs of the needle electrodes. This enables the operator to selectively position the electrodes surrounding a selected tissue and to selectively apply the direction of the electrical field as desired for optimum treatment. The rotor 108 enables the field to be selectively generated around or across the tissue from all directions.

Figure 7:
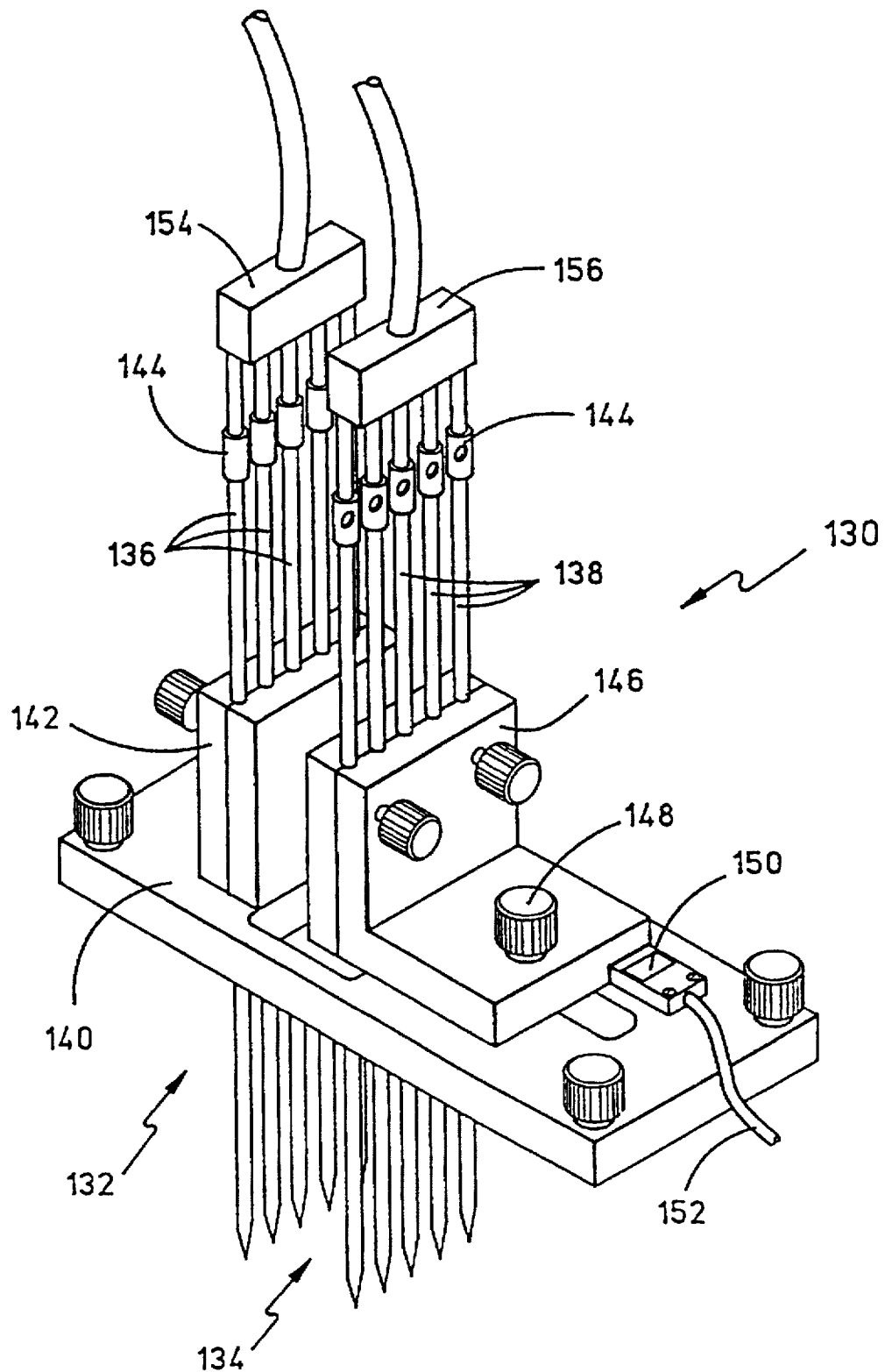
FIG. 7 is a perspective view of a further embodiment of the invention.

Referring to FIG. 7 an alternate embodiment of an electric field generating array of parallel adjustably positionable electrodes, as disclosed in the parent application, is illustrated. The electric assembly designated generally by the numeral 130 includes a pair of spaced apart arrays 132 and 134 of conductive needle electrodes 136 and 138 mounted on a dielectric carrier or support member 140. The needle array 132 is held in a fixed clamp 142 which allows the needles 136 to be adjusted in depth relative to the support 140.

The needles 138 are mounted in a mountable clamp 146 which is adjustably mounted on support member 140 by a clamp screw 148. The needles 136 and 138 are each provided with a penetration stop 144. The gap spacing clamp 148 secures the clamp 146 in selected positions on the support 140. A gap spacing sensor 150 senses the distance between the needle arrays 132 and 134 and generates a signal that is sent to the pulse generator via conductor cable 152. A pulse generator is connected to the needle electrodes by means of cables 154 and 156.

In operation, a unit as above described is selected and mounted on suitable support such as a suitable clamp and articulated arm assembly not shown. The support is positioned over the patient and the needles of the array are inserted into one side of a selected tissue of a patient. The electrodes are positioned at another side of the tissue to be treated and inserted into the tissue. Anticancer drugs are infused or injected into the patient by a syringe or other suitable means. The drugs or other molecules may be injected into the blood stream or directly into the tumor or other tissue being treated.

Figure 8:
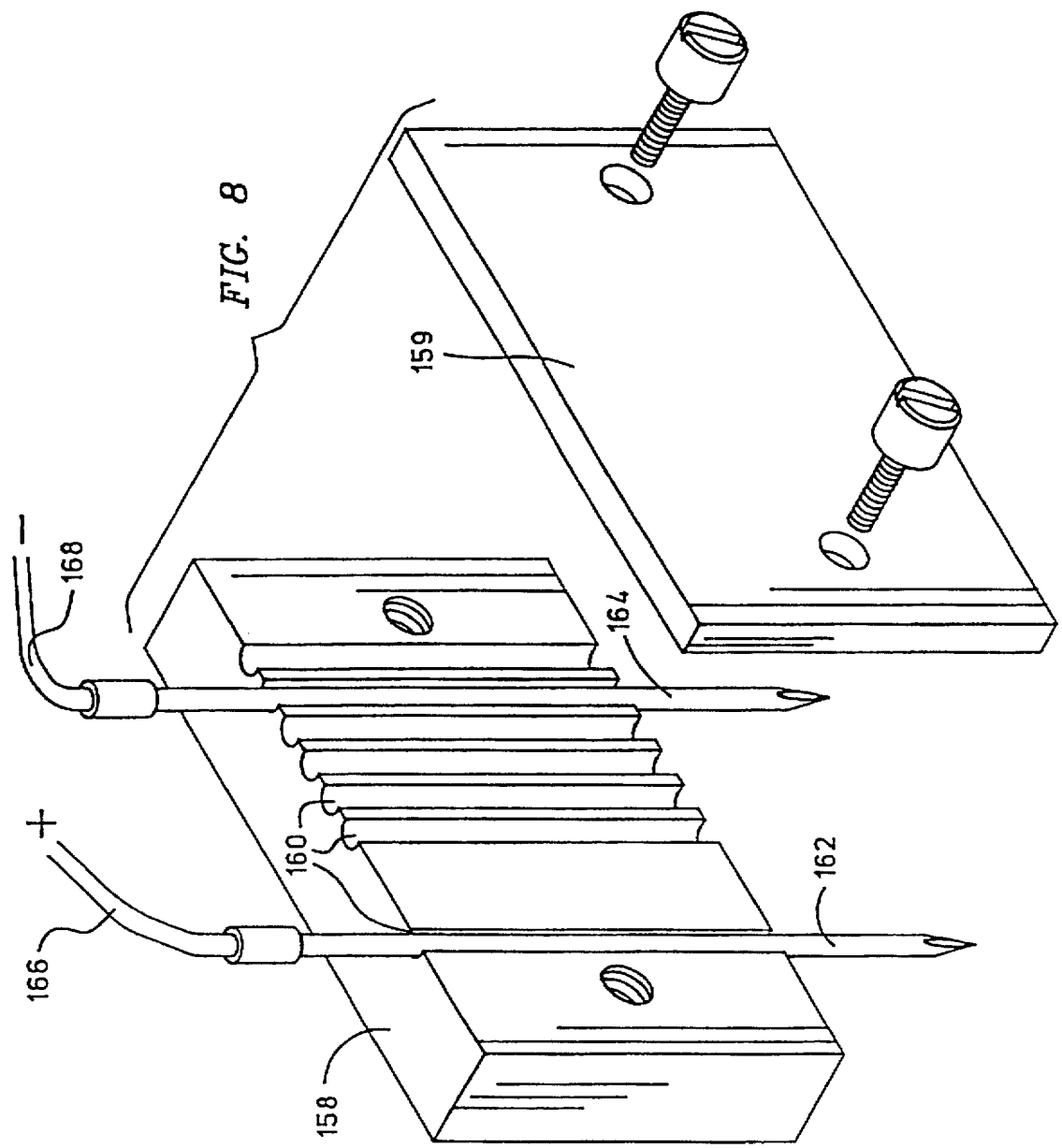
FIG. 8 is a perspective view of a still further embodiment of the invention.

Referring to FIG. 8, details of a needle holder or template for various arrangements for establishing a spaced pair or parallel arrays of needles is illustrated. This embodiment comprises a base holder member 158 having a plurality of adjacently positioned parallel slots 160 into which selected needles 162 and 164 may be positioned in selected spaced relation. This holder may serve to mount a pair of oppositely polarized needle electrodes 162 and 164, as illustrated. These can be selectively positioned in selected space relationship to be disposed on opposite sides of a selected tissue. The needles are clamped into the slots by a clamp or plate 159. In addition, the holder may be used in combination with an additional holder for provision of multiple arrays on opposite sides of a selected tissue. The illustrated needles may be connected by conductors 166 and 168 to a suitable pulse generator.

Figure 9A:
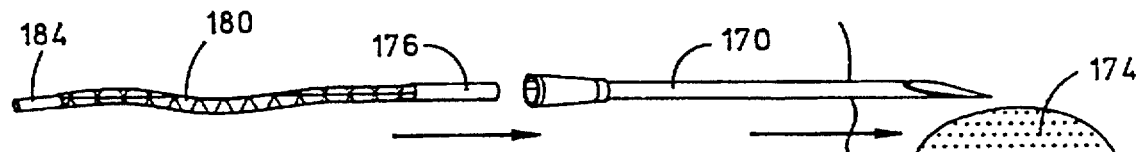
FIGS. 9a–9d is a top plan view, illustrating a preferred form of electrodes and sequence of use.
Figure 9B:
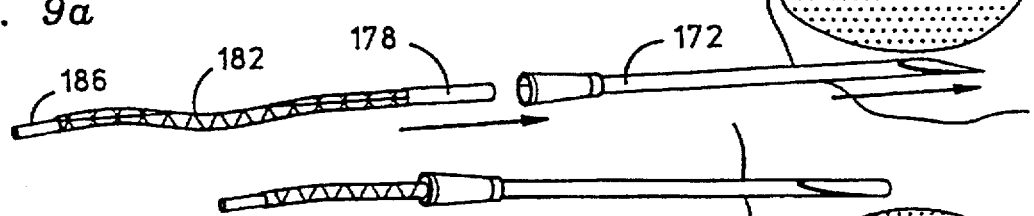
Figure 9C:
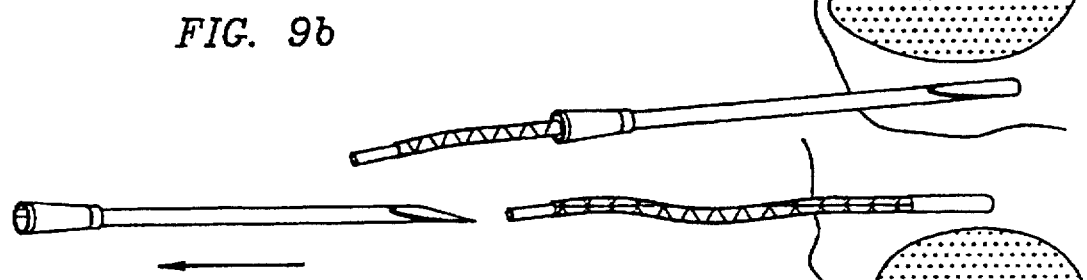
Figure 9D:
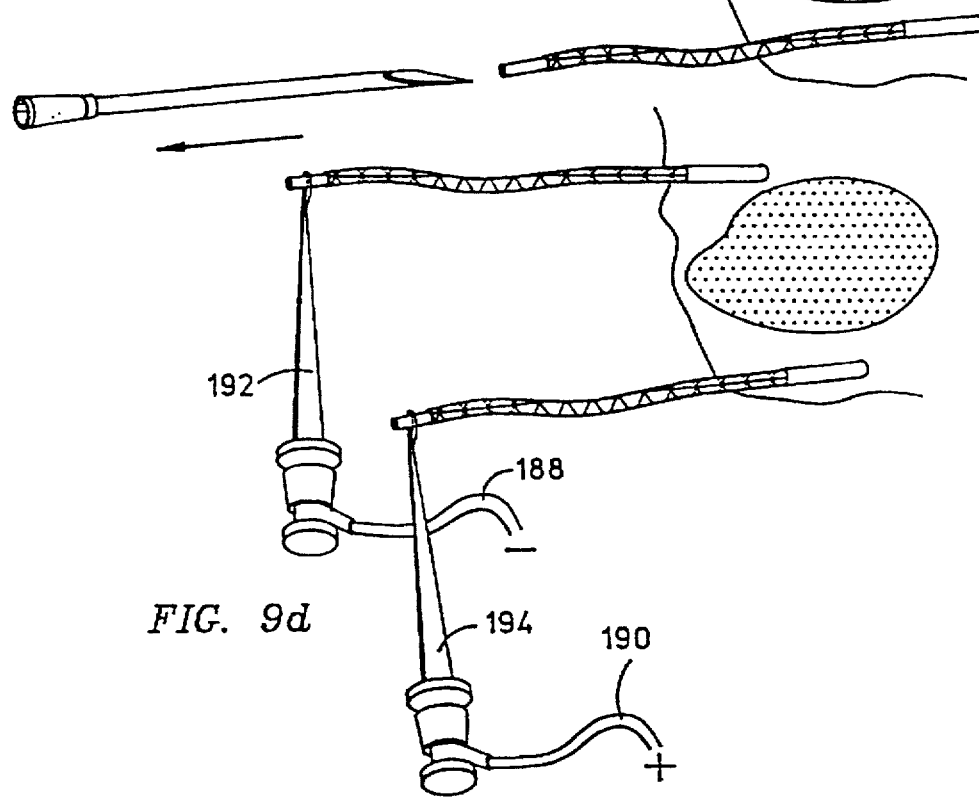

Referring to FIGS. 9a through 9d, an additional aspect of the invention is illustrated. As more clearly illustrated, the combination electrodes may take the form of separate needles 170 and 172 which may be first inserted beside a selected area such as on opposite sides of a tumor as illustrated. Thereafter the needles may be connected to a syringe or other source of molecules and used to inject a selected molecular solution into the tissue area. The needles may be non-conductive and a pair of electrodes 176 and 178, as illustrated in FIG. 9b, are selectively fed through the bore or lumen of the respective needles into the tissue, as illustrated, and thereafter the needle is removed, as shown in FIG. 9c. The electrodes 176 and 178 are each provided with an elongated insulated conductor with conductive tips 184 and 186.

A pair of conductors 188 and 190 from a suitable power generator may then be connected to the ends of the conductors of the electrodes by micro clamps 192 and 194, as shown in 9d, and an electric potential applied across the electrodes. This generates a field in the tissue and electroporates the cells of the selected tissue, such as a tumor or the like. This enables the selected molecules to enter the cells of the tissue and more efficiently kill or alter the cells as desired. This form of needle and electrode may be used with all the above described assemblies.

These needle electrode assemblies, as above described, enable the in vivo positioning of electrodes in or adjacent to subsurface tumors or other tissue. While the focus of the present application has been on electrochemotherapy, the embodiment of the subject invention may be applied to the treatment, such as gene therapy of certain organs of the body.

The nature of the electric field to be generated is determined by the nature of the tissue, the size of the selected tissue and its location. It is desirable that the field be as homogenous as possible and of the correct amplitude. Excessive field strength results in lysing of cells, whereas a low field strength results in reduced efficacy.

The waveform of the electrical signal provided by the pulse generator can be an exponentially decaying pulse, a square pulse, a unipolar oscillating pulse train or a bipolar oscillating pulse train. The electric field strength can be 0.2 kV/cm to 20 kV/cm. The pulse length can be ten μ to 100 ms. There can be one to one hundred pulses. Of course, the waveform, electric field strength and pulse duration are also dependent upon the type of cells and the type of molecules that are to enter the cells via electroporation.

The various parameters including electric field strengths required for the electroporation of any known cell is generally available from the many research papers reporting on the subject, as well as from a database maintained by Genetronics, Inc., San Diego, Calif., assignee of the subject application. The electric fields needed for in vivo cell electroporation, such as ECT, are similar in amplitude to the fields required for cells in vitro. These are in the range of from 100 V/cm to several kV/cm. This has been verified by the inventors own experiments and those of others reported in scientific publications. The first in vivo application of pulsed electric fields in the chemotherapy field to treat tumors was reported in 1987 by Okino in Japan.

Pulse generators for carrying out the procedures described herein are and have been available on the market for a number of years. One suitable signal generator is the ELECTRO CELL MANIPULATOR Model ECM 600 commercially available from GENETRONICS, INC. of San Diego, Calif., U.S.A. The ECM 600 signal generator generates a pulse from the complete discharge of a capacitor which results in an exponentially decaying waveform. The electric signal generated by this signal generator is characterized by a fast rise time and an exponential tail. In the signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads).

The ECM 600 signal generator has a control knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600 signal generator. This device further includes a plurality of push button switches for controlling pulse length, in the Low VM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the flow-through chamber is an automatic cycle that takes less than five seconds. The manual button may be sequentially pressed to repeatedly apply the predetermined electric field.

While I have illustrated and described my invention by means of specific embodiments, it is to be understood that numerous changes and modifications may be made therein without departing from the spirit and the scope of the invention as defined in the appended claims.

I claim:

1. An electrode apparatus for the application of electric fields to a selected portion of a living body, comprising:
   support means;
   an array of multiple opposed pairs of electrodes mounted on said support means in spaced relation to one another, at least one of said pairs of electrodes having a needle configuration for penetrating tissue for in vivo electroporation of cells of the tissue; and
   an electric pulse generator for applying pulses of high amplitude electric signals to selected opposed pairs of said electrodes proportionate to the distance between said electrodes for electroporation of cells between said electrodes.

2. An apparatus according to claim 1 wherein one of said needle electrodes having a cannula for the introduction of molecules into said tissue.

3. An apparatus according to claim 2 wherein said support means comprises a hub mounted on said support and said electrodes are a circular array of needles supported on said hub.

4. An apparatus according to claim 1 wherein said support means comprises a hub mounted on a shaft and said electrodes are needles in a circular array supported on said hub.

5. An apparatus according to claim 4 wherein said apparatus includes a rotary switch selectively positionable for connecting alternate opposite pairs of electrodes to said pulse generator.

6. An apparatus according to claim 1 wherein the field generator generates an electric field having a strength of between approximately 0.2 kV/cm and 20 kV/cm and between approximately one pulse and one hundred pulses for application to a tissue.

7. An electrode apparatus for the application of electric fields to a selected portion of a living body, comprising:
   support means;
   an array of electrodes mounted on said support means in spaced relation to one another, at least a plurality of said electrodes having a needle configuration for penetrating tissue for in vivo electroporation of cells of the tissue; and
   an electric pulse generator for applying pulses of high amplitude electric signals to the electrodes proportionate to the distance between said electrodes for electroporation of cells between said electrodes, wherein said array of electrodes comprises a circular array of needle electrodes, and a switch assembly for selectively changing the polarity of opposing ones of said electrodes.

8. An apparatus according to claim 7 wherein at least one of said needle electrodes has a cannula for injecting molecules into said tissue.

9. An apparatus according to claim 7 wherein said electrodes comprises a pair of tubular needles for inserting into selected tissue, and conductors insertable through said needles into said tissue.

10. An apparatus according to claim 9 wherein said needles are removable over said conductors.

11. A needle electrode assembly of needle electrodes for the application of electric fields to a selected portion of a living body, comprising:
    a first combination needle electrode for insertion into selected tissue for injecting molecules into said tissue and for functioning as a first electrode;
    a second combination of multiple needle electrodes for insertion into said selected tissue spaced from said first electrode, at least one of said multiple electrodes functioning as a second electrode in relation to said first electrode; and
    means for selectively connecting multiple pairs of said needle electrodes in pairs of opposed polarity to an electric pulse generator for applying pulses of high amplitude electric signals to the electrodes proportionate to the distance between said electrodes for in vivo electroporation of cells between said electrodes.

12. An apparatus according to claim 11 wherein said first and one of paid second needle electrodes comprises a pair of tubular needles for inserting into selected tissue, and said electrodes are separable conductors insertable through said needles into said tissue.

13. An apparatus according to claim 12 wherein said needles are removable over said electrodes.

14. An apparatus according to claim 11 further comprising switching means selectively positionable for connecting alternate opposite pairs of electrodes to said pulse generator.

15. An electrode apparatus for the application of electric fields to a selected portion of a living body, comprising:
    an array of multiple pairs of electrodes at least multiple pairs of said electrodes having a needle configuration for penetrating selected tissue in spaced relation for in vivo electroporation of cells of the tissue; and
    an electric pulse generator for selectively applying pulses of high amplitude electric signals to selected opposed pairs of said electrodes proportionate to the distance between said selected pairs of electrodes for electroporation of cells between said selected pairs of electrodes.

16. An apparatus according to claim 15 wherein said pairs of needle electrodes comprises a pair of tubular needles for inserting into selected tissue, and separable conductors insertable through said needles into said tissue.

17. An apparatus according to claim 16 wherein said needles are removable over said conductors.

18. An apparatus according to claim 15 further comprising switch means selectively positionable for connecting alternate opposite pairs of electrodes to said pulse generator.

* * * * *

UNITED STATES PATENT AND TRADEMARK OFFICE
CERTIFICATE OF CORRECTION

PATENT NO. : 5,702,359
DATED : December 30, 1997
INVENTOR(S) : Hofmann et al.

It is certified that error appears in the above-indentified patent and that said Letters Patent is hereby corrected as shown below:

In the Abstract, delete beginning on line 3 "member . . ." through line 11 ending with "electrodes", and insert on line 2 after "support" --, an array of electrodes mounted on the support in spaced relation to one another, at least one of the electrodes having a needle configuration for penetrating tissue for in vivo electroporation of cells of the tissue, and an electric pulse generator for applying pulses of high amplitude electric signals to the electrodes proportionate to the distance between opposing ends of the electrodes for electroporation of cells between said electrodes. --

Signed and Sealed this

Sixteenth Day of June, 1998

*Attest:*

BRUCE LEHMAN

*Attesting Officer*  *Commissioner of Patents and Trademarks*

US005702359C1

(12) EX PARTE REEXAMINATION CERTIFICATE (5311st)
United States Patent
Hofmann et al.

(10) Number: US 5,702,359 C1
(45) Certificate Issued: Mar. 28, 2006

(54) NEEDLE ELECTRODES FOR MEDIATED DELIVERY OF DRUGS AND GENES

(75) Inventors: Gunter A. Hofmann, San Diego, CA (US); Richard A. Gilbert, Tampa, FL (US); Yasuhiko Hayakawa, Ichikawa (JP); Richard Heller, Brandon, FL (US); Mark J. Jaroszeski, Tampa, FL (US)

(73) Assignee: Genetronics, Inc., San Diego, CA (US)

Reexamination Request:
No. 90/005,590, Dec. 15, 1999

Reexamination Certificate for:
Patent No.: 5,702,359
Issued: Dec. 30, 1997
Appl. No.: 08/467,566
Filed: Jun. 6, 1995

Certificate of Correction issued Jun. 16, 1998.

Related U.S. Application Data

(63) Continuation-in-part of application No. 08/042,039, filed on Apr. 1, 1993, now Pat. No. 5,439,440.

(51) Int. Cl.
*A61N 1/30* (2006.01)

(52) U.S. Cl. .................. 604/20; 607/116; 607/148; 604/21
(58) Field of Classification Search .............. 604/20–21; 607/116–117, 37, 53–54, 148; 435/285.2, 435/173.6
See application file for complete search history.

(56) References Cited

U.S. PATENT DOCUMENTS 3,773,051 A * 11/1973 Holcomb et al. ........... 327/172
5,036,850 A * 8/1991 Owens ........................ 607/46
5,097,833 A * 3/1992 Campos ...................... 607/46
5,273,525 A    12/1993 Hofmann .................... 604/21
5,318,514 A * 6/1994 Hofmann
5,389,069 A    2/1995 Weaver ....................... 604/21
5,411,525 A * 5/1995 Swanson et al. .............. 607/5
5,439,440 A * 8/1995 Hofmann
5,507,781 A * 4/1996 Kroll et al. ..................... 607/5
5,674,267 A    10/1997 Mir et al. ..................... 607/72

FOREIGN PATENT DOCUMENTS

WO    WO 94/22526    10/1984

OTHER PUBLICATIONS

Okino and Mohri, "Effects of a High–Voltage Electrical Impulse and An Anticancer Drug on In Vivo Growing Tumors", *Jpn. J. Cancer Res.* 78:1319–1321 (1987).

Okino and Esato, "The Effects of a Single High Voltage Electrical Stimulation with an Anticancer Drug on in vivo Growing Malignant Tumors", *Jpn. J. Surgery* 20(2):197–204 (1990).

* cited by examiner

*Primary Examiner*—Mark Bockelman

(57) ABSTRACT

An electrode apparatus for the application of electroporation to a portion of the body of a patient, comprises a support, an array of electrodes mounted on the support in spaced relation to one another, at least one of the electrodes having a needle configuration for penetrating tissue for in vivo electroporation of cells of the tissue, and an electric pulse generator for applying pulses of high amplitude electric signals to the electrodes proportionate to the distance between opposing ends of the electrodes for electroporation of cells between said electrodes.

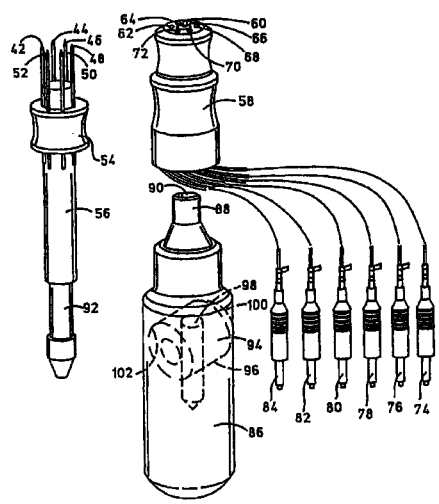

US 5,702,359 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 26–32:

An electrical connector socket assembly comprises a body member 58 having a central opening or bore 60 for receipt of shaft 56 and an annular array of a plurality of sockets 62 through 72 for receipt of the ends of needles 42 through 52. The sockets 62 through 72 electrically connect the needles to leads 74 through 84 which connect to *switching means in the form of* a distributing switch, as will be subsequently described.

Column 4, line 51 to Column 5, line 15:

The holder when assembled as shown in FIG. 4 may be grasped in the hand and the needles inserted into a selected tissue area. The needles 42–52 are preferably spaced and positioned to surround the selected tissue of treatment. One or more of the needles 42–52, as previously explained, may be hollow to enable the injection of the desired medication. The electrode leads 74–84 are then connected in a preferred arrangement to *switch means such as* a rotable switch assembly, as shown in FIG. 5, which enables the selection of opposed pairs of the needles for activation or the application of the electrical potential *simultaneously*.

The switch assembly designated generally by the numeral 104 comprises a stationary housing 106 which, in the illustrated embodiment, is generally cylindrical in configuration and in which is mounted a rotor 108 with spaced contacts 110 and 112 connected by a pair of conductors 114 and 116 to a pulse power generator 115. The rotor contacts 110 and 112 are positioned within housing 106 to engage annular contacts 118, 120, 122, 124, 126 and 128 to which leads 74–84 are connected.

Referring to FIGS. 6a, b and c, the rotor 108 has an internal portion having contacts 110 and 112 each of which bridge between two contacts 118–128 to which the leads 74 through 84 are connected to connect the source of power. The internal contacts 110 and 112 rotate with the rotor 108 and can be selectively positioned in conductive relation with *two opposed* pairs of the internal contacts 118–128 to thereby activate opposed pairs of the needle electrodes *simultaneously*. This enables the operator to selectively position the electrodes surrounding a selected tissue and to selectively apply the direction of the electrical field *between two opposed pairs of electrodes* as desired for optimum treatment. The rotor 108 enables the field to be selectively generated around or across the tissue from all directions.

AS A RESULT OF REEXAMINATION, IT HAS BEEN DETERMINED THAT:

Claims 1, 2, 5–7, 9, 11, 12, 14–16 and 18 are determined to be patentable as amended.

Claims 3, 4, 8, 10, 13 and 17, dependent on an amended claim, are determined to be patentable.

1. An electrode apparatus for the application of electric fields to a selected portion of a living body, comprising:

support means;

an array of multiple opposed pairs of electrodes mounted on said support means in spaced relation to one another, at least one of said pairs of electrodes having a needle configuration for penetrating tissue for in vivo electroporation of cells of the tissue; [and]

an electric pulse generator *for generating electroporation pulses; and* a switch assembly for connecting at least two opposed pairs of said electrodes to said pulse generator for applying pulses of high amplitude electric signals to [selected] *both of said* opposed pairs of said electrodes simultaneously to generate electric fields proportionate to the distance between said electrodes for electroporation of cells between said electrodes, *wherein the switch assembly is capable of connecting said multiple opposed electrodes to said electric pulse generator in at least three different pulsing configurations.*

2. An apparatus according to claim 1 wherein one of said needle electrodes [having] *has* a cannula for the introduction of molecules into said tissue.

5. An *electrode* apparatus [according to claim 4 wherein said apparatus includes] *for the application of electric fields to a selected portion of a living body, comprising:*

*support means;*

*an array of multiple opposed pairs of electrodes mounted on said support means in spaced relation to one another, wherein said support means comprises a hub mounted on a shaft and said electrodes are needles in a circular array supported on said hub for penetrating tissue for in vivo electroporation of cells of the tissue;*

*an electric pulse generator for generating electroporation pulses; and* a rotary switch selectively positionable for connecting *at least two* alternate [opposite] *opposed* pairs of electrodes to said pulse generator *for applying pulses of high amplitude electric signals to both of said opposed pairs of said electrodes to generate electric fields proportionate to the distance between said electrodes for electroporating cells postioned between said electrodes.*

6. An apparatus according to claim 1 wherein the [field] *electric pulse* generator generates an electric field having a strength of between approximately 0.2 kV/cm and 20 kV/cm and between approximately one pulse and one hundred pulses for application to a tissue.

7. An electrode apparatus for the application of electric fields to a selected portion of a living body, comprising:

support means;

an array of electrodes mounted on said support means in spaced relation to one another, at least a plurality of said electrodes having a needle configuration for penetrating tissue for in vivo electroporation of cells of the tissue; and an electric pulse generator for applying pulses of high amplitude electric signals to the electrodes proportionate to the distance between said electrodes for electroporation of cells between said electrodes, wherein said array of electrodes comprises a circular array of needle electrodes, and a switch assembly for [selectively changing the polarity of opposing ones] *connecting at least two opposed pairs* of said electrodes *to said pulse generator for applying electric signals to both of* said opposed pairs simultaneously and to permit changing the polarity of electrodes within each of the at least two opposed pairs.

9. An *electrode* apparatus [according to claim 7] *for the application of electric fields to a selected portion of a living body, comprising:*

*support means;*

*an array of electrodes mounted on said support means in spaced relation to one another, at least a plurality of said electrodes having a needle configuration for penetrating tissue in vivo for electroporation of cells of the tissue,* wherein said electrodes comprise[s] a pair of tubular needles for inserting into selected tissue, and conductors insertable through said needles into said tissue; *and*

*an electric pulse generator for applying pulses of high amplitude electric signals to the electrodes proportionate to the distance between said electrodes for electroporation of cells between said electrodes,* wherein said array of electrodes comprises a circular array of needle electrodes, and a switch assembly for connecting at least two opposed pairs of said electrodes to said pulse generator for applying electric signals to both of said opposing pairs simultaneously and to permit changing the polarity of electrodes within each of the at least two opposed pairs.

11. A needle electrode assembly of needle electrodes for the application of electric fields to a selected portion of a living body, comprising:

a first combination needle electrode for insertion into selected tissue for injecting molecules into said tissue and for functioning as a first electrode;

a second combination of multiple needle electrodes for insertion into said selected tissue spaced from said first electrode, at least one [of said multiple electrodes] *for* functioning as a second electrode in relation to said first electrode; and means for selectively connecting [multiple pairs] *at least two opposed pairs* of said needle electrodes[in pairs of opposed], *wherein the two electrodes in a pair have opposite* polarity, to an electric pulse generator [for] *to permit* applying pulses of high amplitude electric signals to *both of the least two opposed pairs of* the electrodes *simultaneously to generate electric fields* proportionate to the distance between said electrodes for in vivo electroporation of cells between said electrodes; *wherein different electrode pair combinations may be selectively connected.*

12. [An apparatus according to claim 11] *A needle electrode assembly for the application of electric fields to a selected portion of a living body, comprising:*

*a first combination needle electrode for insertion into selected tissue for injecting molecules into said tissue and for functioning as a first electrode;*

*a second combination of multiple needle electrodes for insertion into said selected tissue spaced from said first electrode, at least one for functioning as a second electrode in relation to said first electrode,* wherein said first and one of said second needle electrodes comprises a pair of tubular needles for inserting into selected tissue, and said electrodes are separable conductors insertable through said needles into said tissue; *and*

*means for selectively connecting at least two opposed pairs of said needle electrodes, wherein the two electrodes in a pair have opposite polarity, to an electric pulse generator to permit applying pulses of high amplitude electric signals to both of the at least two opposed pairs of the electrodes simultaneously to generate electric fields proportionate to the distance between said electrodes for in vivo electroporation of cells between said electrodes.*

14. An apparatus according to claim 11 [further comprising] *wherein said means for selectively connecting comprises* switching means selectively positionable for connecting alternate opposite pairs of electrodes to said pulse generator.

15. An electrode apparatus for the application of electric fields to a selected portion of a living body, comprising:

an array of multiple pairs of electrodes, at least multiple pairs of said electrodes having a needle configuration for penetrating selected tissue in spaced relation for in vivo electroporation of cells of the tissue; [and]

an electric pulse generator *for generating electroporation pulses;* and means for selectively *connecting at least two opposed pairs of said electrodes to said pulse generator to permit* applying pulses of high amplitude electric signals to [selected] *both of said* opposed pairs of said electrodes *simultaneously to generate electric fields* proportionate to the distance between said [selected] pairs of electrodes for [electroporation of] *electroporating* cells between said [selected] pairs of electrodes, *wherein different electrode pair combinations may be selectively connected.*

16. An *electrode* apparatus [according to claim 15] *for the application of electric fields to a selected portion of a living body, comprising:*

*an array of multiple pair of electrodes, at least multiple pairs of said electrodes having a needle configuration for penetrating selected tissue in spaced relation for in vivo electroporation of cells of the tissue,* wherein said pairs of needle electrodes comprises a pair of tubular needles for inserting into selected tissue, and separable conductors insertable through said needles into said tissue;

*an electric pulse generator for generating electroporation pulses; and*

*means for selectively connecting at least two opposed pairs of said electrodes to said pulse generator for applying pulses of high amplitude electric signals to both of said opposed pairs of said electrodes simultaneously to generate electric fields proportionate to the distance between said pairs of electrodes for electroporating cells between said pairs of electrodes.*

18. An apparatus according to claim 15 [further comprising] *wherein said means for selectively connecting comprises a* switch [means] selectively positionable for connecting alternate opposite pairs of electrodes to said pulse generator.

* * * * *